(12) United States Patent
Nicholls et al.

(10) Patent No.: US 9,759,644 B2
(45) Date of Patent: Sep. 12, 2017

(54) BALANCED CAPILLARY BRIDGE VISCOMETER

(75) Inventors: Mark Nicholls, Houston, TX (US); Michael P. Murphy, West Conroe, TX (US)

(73) Assignee: Malvern Instruments Incorporated, Westborough, MA (US)

(*) Notice: Subject to any disclaimer, the term of this patent is extended or adjusted under 35 U.S.C. 154(b) by 260 days.

(21) Appl. No.: 13/825,622

(22) PCT Filed: Sep. 23, 2011

(86) PCT No.: PCT/GB2011/051805
§ 371 (c)(1),
(2), (4) Date: Nov. 18, 2013

(87) PCT Pub. No.: WO2012/038762
PCT Pub. Date: Mar. 29, 2012

(65) Prior Publication Data
US 2014/0144214 A1 May 29, 2014

Related U.S. Application Data

(60) Provisional application No. 61/385,952, filed on Sep. 23, 2010.

(51) Int. Cl.
*G01N 11/04* (2006.01)
*G01N 11/08* (2006.01)
*G01N 11/02* (2006.01)

(52) U.S. Cl.
CPC ............. *G01N 11/08* (2013.01); *G01N 11/02* (2013.01); *G01N 11/04* (2013.01)

(58) Field of Classification Search
CPC ............. G01N 11/08; G01N 7/08; G01N 7/10
See application file for complete search history.

(56) References Cited

U.S. PATENT DOCUMENTS 2,449,067 A * 9/1948 Guillemin, Jr. ............... 73/23.21
3,086,386 A * 4/1963 Frederick ....................... 73/23.2
(Continued)

FOREIGN PATENT DOCUMENTS

| JP | S59160740 | 10/1983 |
|---|---|---|
| JP | 2006276018 | 10/2006 |
| JP | 2009-133726 | 6/2009 |

OTHER PUBLICATIONS

PCT International Search Report, Dec. 21, 2011.
PCT Written Opinion, Dec. 21, 2011.
Japanese Office Action, dated Apr. 25, 2016.

*Primary Examiner* — Paul West
(74) *Attorney, Agent, or Firm* — Kristofer E. Elbing

(57) ABSTRACT

A capillary bridge viscometer, comprises an input port (flow in) an output port (flow out) a first capillary tubing arm (R1) in a first hydraulic path between the input port and a first differential detection point (DP+), a second capillary tubing arm (R3) in a second hydraulic path between the first differential detection point (DP+) and the output port (flow out), a third capillary tubing arm (R2) in a third hydraulic path between the input port (flow in) and a second differential detection point (DP−), a fourth capillary tubing arm (R4) in a fourth hydraulic path between the second differential detection point (DP−) and the output port (flow out), an adjustable mechanical flow restrictor (20) in one of the first, second, third, and fourth hydraulic paths, wherein the adjustable mechanical flow restrictor (20) is operative to mechanically adjust a resistance to flow of a fluid while the fluid flows through the adjustable mechanical flow restrictor.

22 Claims, 2 Drawing Sheets

(56) References Cited

U.S. PATENT DOCUMENTS

| | | | | |
|---|---|---|---|---|
| 3,302,448 | A | * | 2/1967 | Mocker ........................ 73/31.04 |
| 4,463,598 | A | | 8/1984 | Haney |
| 4,779,642 | A | * | 10/1988 | Wood ................... G05D 16/202 |
| | | | | 137/487.5 |
| 6,561,480 | B1 | * | 5/2003 | Komiya .................... F16K 1/38 |
| | | | | 251/122 |
| 7,213,439 | B2 | | 5/2007 | Trainoff |
| 7,331,218 | B2 | | 2/2008 | Trainoff |
| 2002/0166367 | A1 | | 11/2002 | Bures |
| 2007/0068229 | A1 | | 3/2007 | Trainoff |

\* cited by examiner

BALANCED CAPILLARY BRIDGE VISCOMETER

This application is a US National Stage counterpart of PCT/GB2011/051805 and claims priority to provisional application No. 61/385,952, filed Sep. 23, 2010.

FIELD OF THE INVENTION

The invention relates, in one general aspect, to capillary viscometers, including capillary bridge viscometers that include an automatic balancing mechanism.

BACKGROUND OF THE INVENTION

Referring to FIG. 1, multi-capillary viscometers can introduce some type of delay unit in order to make a differential measurement while a sample is being measured. An illustrative prior art four-capillary viscometer 10, for example, includes four pieces of tubing or capillaries connected in a series-parallel configuration to form the hydraulic equivalent of a Wheatstone-Bridge in electronics. These tubing or capillaries in the arms of the bridge are often referred to as R1, R2, R3, and R4 because they are in effect hydraulic resistors. The delay unit 12 is placed in series with one of the capillaries and usually it consists of a column packed with or containing a material or solvent that will delay the sample from reaching a reference capillary while a measurement is taking place. This delay unit should generally provide for sufficient time or volume to accommodate the entire elution volume of the analytical GPC (Gel Permeation Chromatography) column set that is used for the separation analysis. In liquid chromatography there are a vast number of column set configurations, many requiring different delay volumes. Initially, the capillary configuration is arranged such that the "bridge" is "balanced" meaning that the DP+ & DP-- readings are approximately equal.

In the illustrative viscometer, R1, R2, R3, and R4 are capillary tubes of a small diameter giving them a measurable resistance to the solvent flow, and if R1=R2=R3=R4, the differential pressure (DP) output should theoretically be zero. This is the output signal from the bridge and should be within a small percentage of the total pressure across the bridge measured between the two differential measurement points IP+ and IP- when solvent is flowing. This is called the bridge balance and is given by the equation, Balance=4DP/IP-2DP, where DP is the differential signal from the DP+ and DP- readings measured in Pascals and IP is as mentioned above measured in Pascals.

Capillary bridge viscometers are described in more detail, for example, in U.S. Pat. No. 4,463,598 to Haney, which is herein incorporated by reference.

When a delay volume is placed in series with one or more capillaries, the bridge can be balanced or rebalanced to make up for additional resistance introduced by the presence of the delay volume(s). This can be accomplished by adjusting the length(s) of one or more of the capillary tubing runs to get the bridge balance back to the manufacturing standard balance. Upon installation or during use, it may become necessary to adjust this delay volume according to the analytical column set required for analysis. One or more additional delay volumes of different sizes may therefore be shipped with the instrument or purchased to meet the specific need of the customer. With these changes comes either increased or decreased resistance within the combined capillary and delay column flow path, and the viscometer can be rebalanced by adding or subtracting to the length of the appropriate capillary tubing in order to achieve the most efficient performance by returning to a balanced condition.

The traditional method for balancing a viscometer bridge is to change the length of one or more of the capillary flow paths. This is accomplished by calculating the amount to subtract (or add) from a length of one or more of the capillaries. The bridge is then disassembled to make the change and reassembled by a skilled technician. This can be extremely inconvenient and may also require the instrument to be returned to the manufacturer for qualified servicing. It is also common for the balance to change due to the introduction of different solvents. These changes are typically ignored because of the inconvenience and because the length difference involved can be physically too small to allow an accurate adjustment to be accurately accomplished, and the result can be a decrease in instrument performance.

Temperature-based balancing has also been proposed in U.S. Pat. No. 7,213,439 to Trainoff, which is herein incorporated by reference. But this approach can have the potential drawback of causing thermally induced changes to properties of the fluids in the viscometer. Understanding whether such changes are a concern for a particular experimental setup and whether they should possibly be compensated for can introduce the prospect of an undesirable level of theoretical complexity for the end user of the viscometer.

SUMMARY OF THE INVENTION

Several aspects of the invention are presented in this application.

According to a first aspect of the invention, we provide a capillary bridge viscometer, comprising an input port, an output port, a first capillary tubing arm in a first hydraulic path between the input port and a first differential detection point, a second capillary tubing arm in a second hydraulic path between the first differential detection point and the output port, a third capillary tubing arm in a third hydraulic path between the input port and a second differential detection point, a fourth capillary tubing arm in a fourth hydraulic path between the second differential detection point and the output port. The capillary bridge viscometer may include an adjustable mechanical flow restrictor in one of the first, second, third, and fourth hydraulic paths, wherein the adjustable mechanical flow restrictor is operative to mechanically adjust a resistance to flow of a fluid while the fluid flows through the adjustable mechanical flow restrictor.

The adjustable mechanical flow restrictor may comprise a first conduit that is hydraulically connected to a second circuit. The first and second conduit may be connected through a plumbing block. A movable solid core or rod may be threaded through the second conduit. The solid core or rod may be mounted on a linear actuating mechanism.

The adjustable mechanical flow restrictor may be adapted to balance the bridge viscometer by moving the core in or out of the second conduit. The rod is arranged such that the effective diameter of the second conduit is adjusted due to its position within the second conduit.

The apparatus may include a controller having transducers to measure the pressure at two distinct points and may be adapted to generate a driving signal to the actuator.

DETAILED DESCRIPTION OF AN
ILLUSTRATIVE EMBODIMENT

Figure 1:
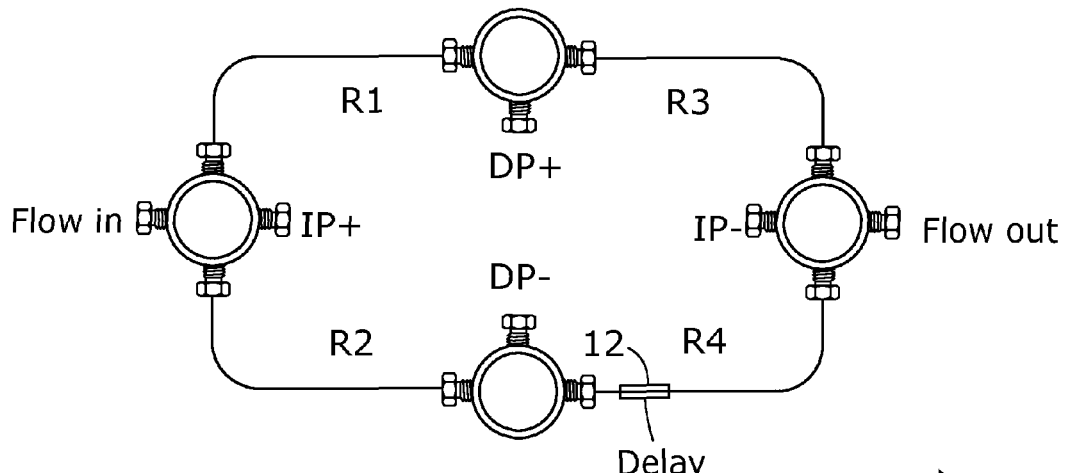
FIG. 1 is a hydraulic schematic diagram of a prior art capillary bridge viscometer.
Figure 2:
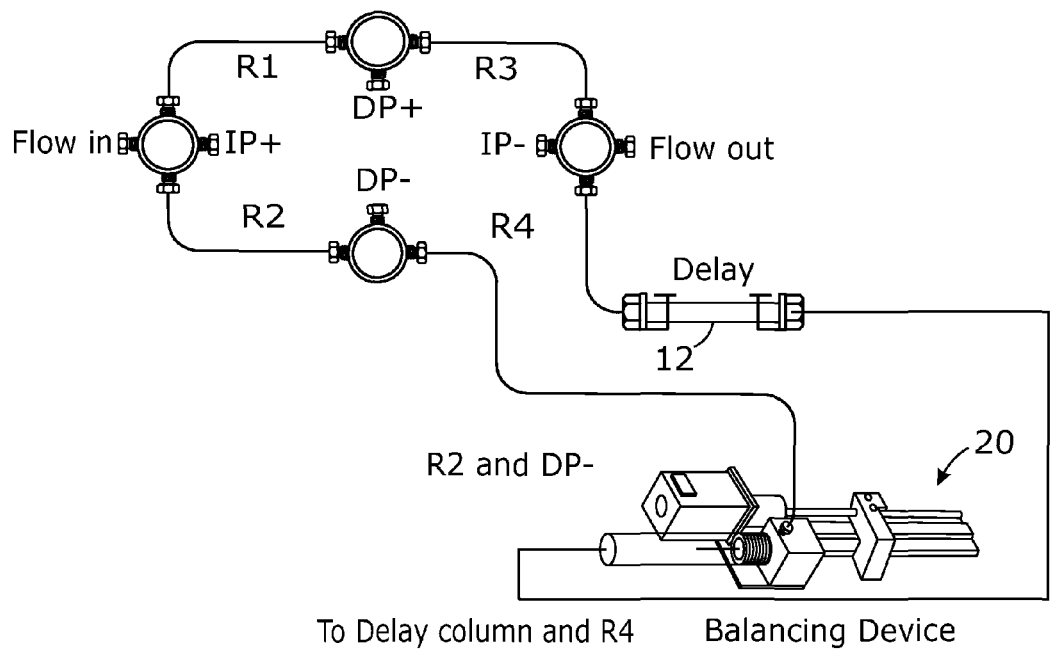
FIG. 2 is a hydraulic schematic diagram of an illustrative capillary bridge viscometer according to the invention.

Referring to FIG. 2, an illustrative capillary bridge viscometer 14 according to the invention includes a bridge 10 with a mechanical balancing unit 20 that can be placed in series with its delay line 12. One of the capillaries is made shorter than it otherwise would at the time of assembly such that the reduction in length is approximately equal to the resistance of the mechanical balancing unit. This allows the illustrative viscometer to overcome normal changes in bridge balance it experiences.

Figure 3:
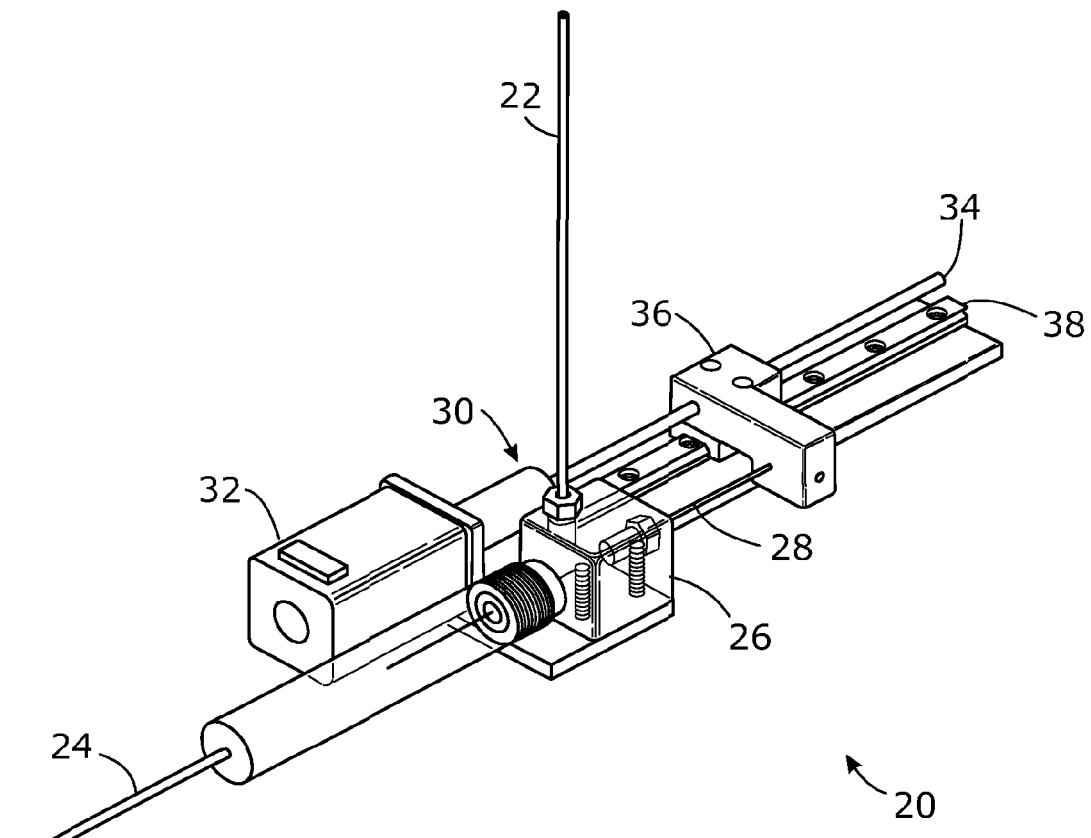
FIG. 3 is a perspective diagram of a mechanical balancing unit for use with the illustrative capillary bridge viscometer of FIG. 2.

Referring to FIG. 3, the mechanical balancing unit 20 includes a first conduit 22 that is hydraulically connected to a second conduit 24, such as through a machined plumbing block 26, which can be made out of a relatively unreactive material such as stainless steel. A movable solid core 28, which can include a straight length of cylindrical Nitinol® rod, is threaded through the second conduit. This second conduit has a calculated diameter large enough to accept the core with the resulting resistance to solvent flow being approximately equal to the corresponding portion of the capillary. The Nitinol rod may be supported by a metal tube to prevent movement and may be sealed to the machined block with a fitting that allows plumbing connection to the rest of the bridge. The Nitinol rod can then be mounted on an actuating mechanism 30, inserted through a seal, and passed into the tubing. The seal can be one of a variety of types of seals, such as an o-ring or seal made with a length of 0.03" Teflon® tubing. The second conduit can be supported by a support structure, such as a threaded aluminum support tube 25.

The actuating mechanism 30 can move the Nitinol rod in and out of the second conduit to change the pressure across the mechanical balancing unit. The actuating mechanism 30 in the illustrative embodiment can be a linear actuating mechanism that includes a motor 32, such as a stepper motor, that drives a lead screw 34 to advance a carriage 36 on a track 38. Other embodiments can employ a variety of other mechanisms to adjust resistance to flow, such as linkages, racks-and-pinions, magnetically coupled linear actuators, or cam-based mechanisms. And while the use of a machined plumbing block with standard fittings is presently preferred to allow movement of the core without leakage, one of ordinary skill in the art would readily recognize that other approaches could also be employed to achieve the same end. The complete assembly can be mounted on a mounting plate for stability.

Figure 4:
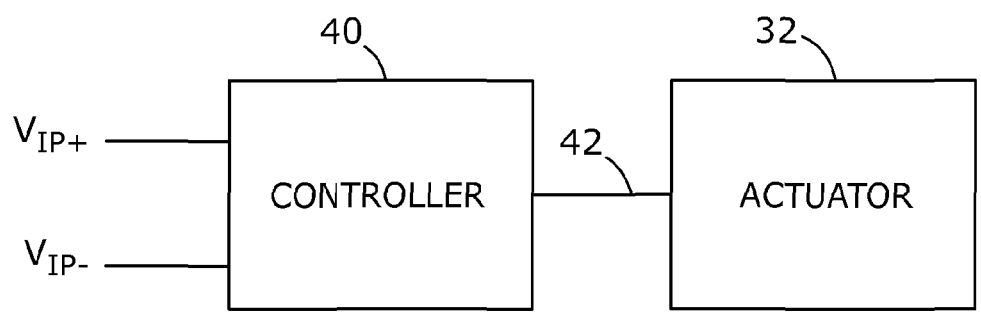
FIG. 4 is a block diagram of a control arrangement for controlling the mechanical balancing unit of FIG. 3.

Referring also to FIG. 4, a controller 40 may be provided to drive the actuator. This controller can employ a variety of known control techniques. It can employ dedicated hard-wired circuitry, software, or a combination of the two.

Operation begins with a solvent being introduced into the bridge viscometer 14. The differential pressure between the two intermediate measurement points DP+ and DP− is measured to determine whether the bridge is in balance. If it is not, the mechanical balancing unit is adjusted by moving the core in or out of the second conduit to balance the bridge.

The Nitinol rod and carriage assembly are situated in relation to the plumbing block such that, when the rod is pulled all the way out, the resistance of the bridge balance device has almost no resistance to fluid flow. As the rod is pushed into the tube the effective diameter of the tube is decreased, which increases the resistance of the flow path containing the device and capillary. This is in essence the same as adding to the length of the capillary. Conversely, drawing the rod back out of the tube reduces the resistance in the flow path containing the device and capillary. This allows the user to obtain excellent precision in viscometer balance and performance.

The adjustment may be performed automatically, semi-automatically, or manually. In automatically balanced embodiments, a controller can detect an imbalance between signals from transducers that measure the two intermediate measurement points DP+ and DP−. The controller can then produce a driving signal 42 that it provides to the actuator 32 until the imbalance is resolved. In semi-automatically balanced embodiments, an operator can provide a signal to the actuator until he or she determines that the bridge is balanced. In a manually balanced embodiment, no actuator is needed and the user can balance the bridge mechanically, such as by manually turning a knob attached to the lead screw 34. All of these methods are less cumbersome than prior art methods that involve replacing lengths of capillary tubing and can be readily performed in situ by the customer.

The mechanical balancing unit mechanism described above has been found to allow very fine pressure adjustments. This can allow for the construction of a highly precise instrument. A variety of other types of balancing unit mechanisms, such as ones based on micrometering valves or ones that that operate by squeezing or stretching flexible tubing, may also be suitable in some circumstances.

The mechanical balancing unit can be used in a variety of different kinds of instruments. It can be used in a more complex capillary viscometer that provides for eliminating break through peaks, for example, such as is described in US Pub. No. 2008/045133 to Titterton, which is herein incorporated by reference. It can also be used in other types of instruments that benefit from the ability to make small changes in flow resistance.

The present invention has now been described in connection with a number of specific embodiments thereof. However, numerous modifications which are contemplated as falling within the scope of the present invention should now be apparent to those skilled in the art. Therefore, it is intended that the scope of the present invention be limited only by the scope of the claims appended hereto. In addition, the order of presentation of the claims should not be construed to limit the scope of any particular term in the claims.

The invention claimed is:

1. A capillary bridge viscometer, comprising:
   an input port,
   an output port,
   a first capillary tubing arm in a first hydraulic path between the input port and a first differential detection point,
   a second capillary tubing arm in a second hydraulic path between the first differential detection point and the output port,
   a third capillary tubing arm in a third hydraulic path between the input port and a second differential detection point,
   a fourth capillary tubing arm in a fourth hydraulic path between the second differential detection point and the output port,
   a delay line in one of the first, second third and fourth hydraulic paths and configured to delay fluid flowing therethrough, wherein the delay line includes a column packed with or containing a material or solvent that will delay the sample, an adjustable mechanical flow restrictor in one of the first, second, third, and fourth hydraulic paths, wherein the adjustable mechanical flow restrictor is operative to mechanically adjust a resistance to flow of a fluid while the fluid flows through the adjustable mechanical flow restrictor, and a second adjustable mechanical flow restrictor in another of the first, second, third, and fourth hydraulic paths, wherein the second adjustable mechanical flow restrictor is operative to mechanically adjust a resistance to flow of a fluid while the fluid flows through the second adjustable mechanical flow restrictor.

2. A capillary bridge viscometer, comprising:
an input port,
an output port,
a first capillary tubing arm in a first hydraulic path between the input port and a first differential detection point,
a second capillary tubing arm in a second hydraulic path between the first differential detection point and the output port,
a third capillary tubing arm in a third hydraulic path between the input port and a second differential detection point,
a fourth capillary tubing arm in a fourth hydraulic path between the second differential detection point and the output port,
a delay line in one of the first, second third and fourth hydraulic paths and configured to delay fluid flowing therethrough, wherein the delay line includes a column packed with or containing a material or solvent that will delay the sample,
an adjustable mechanical flow restrictor in one of the first, second, third, and fourth hydraulic paths, wherein the adjustable mechanical flow restrictor is operative to mechanically adjust a resistance to flow of a fluid while the fluid flows through the adjustable mechanical flow restrictor, wherein the flow restrictor comprises:
a tube having first and second ends and a flow path that follows a fluid flow axis,
a solid, cylindrical core having a first end and a second end, and being slidably mounted with respect to the tube in alignment with the fluid flow axis, and
a translating mechanism coupled to the solid core and operative to adjust the position of the solid core along the fluid flow path in the direction of the fluid flow axis.

3. The apparatus of claim 2 further including an actuator coupled to the adjustable mechanical flow restrictor to adjust the resistance to flow through the adjustable mechanical flow restrictor.

4. The apparatus of claim 3 further including a balance detector operatively connected between the first and second differential detection points.

5. The apparatus of claim 4 further including a balancing controller responsive to the balance detector and operative to actuate the actuator to adjust the resistance to flow through the adjustable mechanical flow restrictor until the capillary bridge viscometer is balanced.

6. The apparatus of claim 2 further including a balance detector operatively connected between the first and second differential detection points.

7. The apparatus of claim 2 wherein the solid core has a range of movement along the flow axis that extends from a first position outside of the first end of the tube to a first position inside of the first end of the tube.

8. The apparatus of claim 2 wherein the tube is cylindrical and the flow axis is located at the center of the tube.

9. The apparatus of claim 2 wherein the translating mechanism includes a motor and a lead screw.

10. The apparatus of claim 2 wherein the delay line is configured to delay a liquid chromatography sample.

11. A capillary bridge viscometer, comprising:
an input port,
an output port,
a first differential pressure detection point,
a second differential pressure detection point,
a first hydraulic path having a first capillary tubing arm between the input port and the first differential pressure detection point,
a second hydraulic path having a second capillary tubing arm between the first differential pressure detection point and the output port,
a third hydraulic path having a third capillary tubing arm between the input port and the second differential pressure detection point,
a fourth hydraulic path having a fourth capillary tubing arm between the second differential pressure detection point and the output port,
an adjustable mechanical flow restrictor in one of the first, second, third, and fourth hydraulic paths, wherein the adjustable mechanical flow restrictor is operative to mechanically adjust a resistance to flow of a fluid while the fluid flows through the adjustable mechanical flow restrictor, and
a delay line in one of the first, second third and fourth hydraulic paths and configured to delay fluid flowing therethrough, wherein the delay line includes a column packed with or containing a material or solvent that will delay the sample,
the adjustable mechanical flow restrictor comprising:
a tube having first and second ends and a flow axis;
a solid core having a first end and a second end, and being slidably mounted with respect to the tube in alignment with the flow axis; and
a translating mechanism coupled to the solid core and operative to adjust the position of the solid core along the flow axis,
wherein the tube has a diameter large enough to accept the solid core such that the resulting resistance to flow of the fluid through the tube is approximately equal to the resistance to flow of the fluid through a corresponding portion of the capillary tubing arm in another of the first, second, third, and fourth hydraulic paths.

12. The apparatus of claim 11 wherein the delay line is in series with the flow restrictor.

13. The apparatus of claim 11 further including an actuator coupled to the adjustable mechanical flow restrictor to adjust the resistance to flow through the adjustable mechanical flow restrictor.

14. The apparatus of claim 11 further including a balance detector operatively connected between the first and second differential pressure detection points.

15. The apparatus of claim 14 further including a balancing controller responsive to the balance detector and operative to actuate the actuator to adjust the resistance to flow through the adjustable mechanical flow restrictor until the capillary bridge viscometer is balanced.

16. The apparatus of claim 11 wherein the solid core has a range of movement along the flow axis that extends from a first position outside of the first end of the tube to a first position inside of the first end of the tube.

17. The apparatus of claim 11 wherein the tube and the core are both cylindrical and the flow axis is located at the center of the tube.

18. The apparatus of claim 11 wherein the translating mechanism includes a motor and a lead screw.

19. The apparatus of claim 11 wherein the delay line is configured to delay a liquid chromatography sample.

20. The apparatus of claim 11 wherein the translating mechanism is operative to adjust the position of the solid core along a fluid flow path that follows the fluid flow axis.

21. A method of operating a capillary bridge viscometer according to claim 11, the method comprising the sequential steps of:
   introducing a fluid into the bridge viscometer through the input port;
   measuring the differential pressure between the first and second differential pressure detection points to determine whether the bridge is in balance; and
   if the bridge is not in balance, adjusting the mechanical flow restrictor to balance the bridge.

22. The method of claim 21 wherein the mechanical flow restrictor is adjusted by a controller detecting an imbalance in the bridge and producing a driving signal to an actuator to adjust the mechanical flow resistor until the balance is resolved.

\* \* \* \* \*